US009226951B2

(12) United States Patent
Liang et al.

(10) Patent No.: US 9,226,951 B2
(45) Date of Patent: *Jan. 5, 2016

(54) ANTI-TUMOR FIBRILLAR HUMAN SERUM ALBUMIN METHODS AND COMPOSITIONS

(71) Applicant: Academia Sinica, Nankang, Taipei (TW)

(72) Inventors: Shu-Mei Liang, Taipei (TW); Chi-Ming Liang, Bethesda, MD (US)

(73) Assignee: ACADEMIA SINICA, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/738,856

(22) Filed: Jan. 10, 2013

(65) Prior Publication Data

US 2013/0123183 A1 May 16, 2013

Related U.S. Application Data

(62) Division of application No. 12/623,162, filed on Nov. 20, 2009, now Pat. No. 8,357,652.

(51) Int. Cl.
| | | |
|---|---|---|
| C07K 14/765 | (2006.01) | |
| A61K 38/38 | (2006.01) | |
| A61K 38/16 | (2006.01) | |
| A61K 47/48 | (2006.01) | |

(52) U.S. Cl.
CPC ............ *A61K 38/385* (2013.01); *A61K 38/162* (2013.01); *A61K 38/38* (2013.01); *A61K 47/48284* (2013.01); *C07K 14/765* (2013.01)

(58) Field of Classification Search
None
See application file for complete search history.

(56) References Cited

U.S. PATENT DOCUMENTS

| 2003/0032017 A1 | 2/2003 | Anderson et al. |
| 2005/0009178 A1 | 1/2005 | Yost et al. |
| 2008/0300186 A1 * | 12/2008 | Liang et al. ............ 514/12 |

FOREIGN PATENT DOCUMENTS

| WO | 9927167 | 6/1999 |
| WO | 9964440 | 12/1999 |
| WO | 0032225 | 6/2000 |
| WO | 0170762 | 9/2001 |
| WO | 2004049819 | 6/2004 |
| WO | 2008093342 | 8/2008 |

OTHER PUBLICATIONS

Taboada et al, American Chemical Society 110:20733-20736, 2006.*
Grinstaff et al, PNAS 88:7708-7710, 1991.*
Stathopulos et al ,Protein Science 13:3017-3027, 2004.*
Bouma; et al."Glycation Induces Formation of Amyloid Cross-B Structure in Albumin", J Biol Chem (Oct. 2003), 278 (43):41810-41819.
Garcia-Briones; et al. "Differential distribution of non-structural proteins of foot-and-mouth disease virus in BHK-21 cells", Virology (Jun. 2006), 349(2):409-421.
Gosal; et al. "Novel Amyloid Fibrillar Networks Derived from a Globular Protein: B-Lactoglobulin", Langmuir (2002), 18(19): 7174-7181.
Guarne; et al. "Structural and Biochemical Features Distinguish the Foot-and-Mouth Disease Virus Leader Proteinase from Other Papain-like Enzymes", J Mol Bio (Oct. 2000), 302(5)1227-1240.
Huang; et al., Albumin fibrillization induces apoptosis via integrin/FAK/Akt pathway, BMC Biotechnol (Jan. 2009), 9:2.
Morgell; et al. "Inclusion Bodies: Specificity in their aggregation process and amyloid-like structures", Biochim Biophys Acta (Oct. 2008),1783(10):1815-1825.
Peng; et al. "VP1 of Foot-and-Mouth Disease Virus Induces Apoptosis via the Akt Signaling Pathway", J Biol Chem (Dec. 2004), 279(50):52168-52174.
Sagis; et al. "Mesoscopic structure and viscoelastic properties of B-lactoglobulin gels at low pH and low ionic strength" Langmuir (2004), 924-927.
Schulze; et al. "Electron microscopy demonstration of fibrillar structures in the foot and mouth disease virus", Arch Exp Veterinarmed (1975), 29(1):121-127.
Sechler; et al. "Altered rate of fibronectin matrix assembly by deletion of the first type III repeats", J Cell Biol (Jul. 1996), 134(2):573-583.
Stathopulos; et al. Sonication of proteins causes formation of aggregates that resemble amyloid, Protein Sci (Nov. 2004), 13(11)3017-3027.
Veerman; et al."Mesostructure of fibrillar bovine serum albumin gels", Intl J. of Biol Macromol (Jan. 2003), 31 (4-5):139-146.
Wang; et al."Induction of immunity in swine by purified recombinant VP1 of foot-and-mouth disease virus", Vaccine (Sep. 2003), 21(25-26):3721-3729.

* cited by examiner

*Primary Examiner* — Lei Yao
(74) *Attorney, Agent, or Firm* — Bozicevic, Field & Francis LLP; Pamela Sherwood

(57) ABSTRACT

Fibrillar human serum albumin was shown to be effective in the treatment of various types of cancers. Methods and compositions are disclosed for using fibrillar human serum albumin as a medicament to treat subjects having cancer.

1 Claim, 14 Drawing Sheets

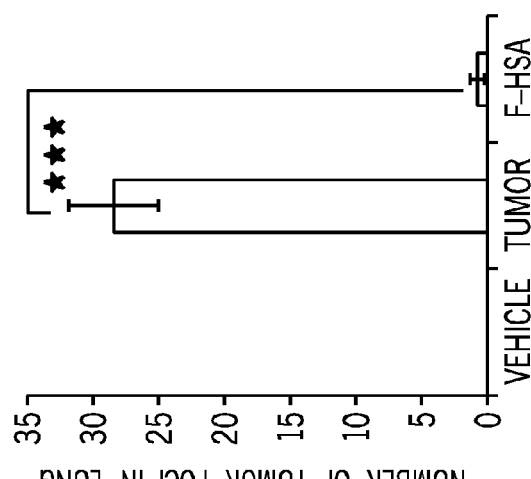
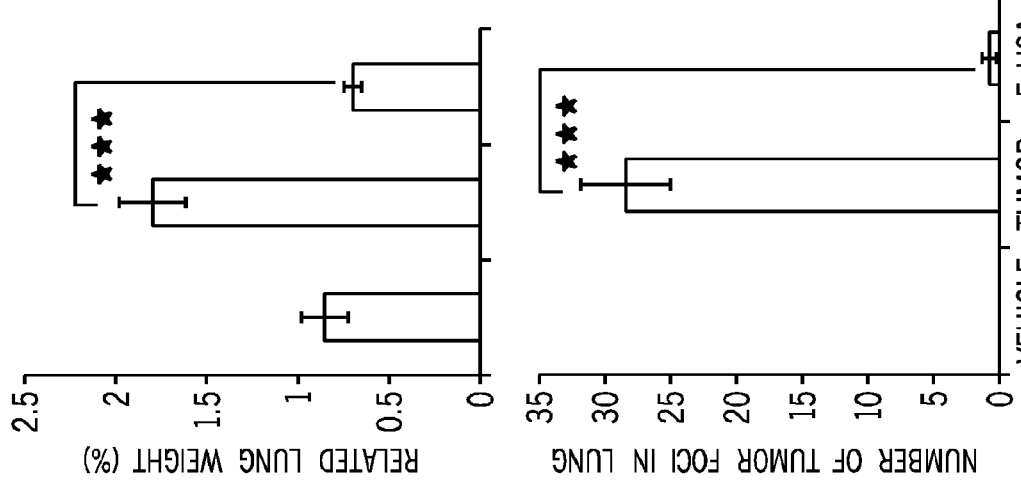
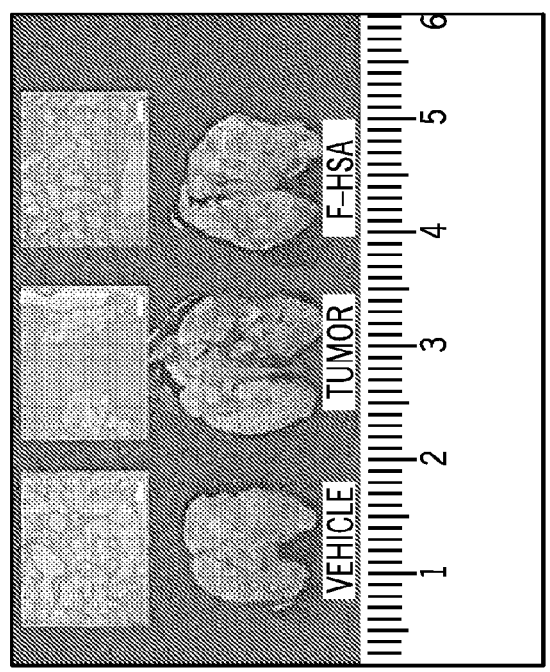

ANTI-TUMOR FIBRILLAR HUMAN SERUM ALBUMIN METHODS AND COMPOSITIONS

This application is a divisional application of U.S. patent application Ser. No. 12/623,162 that has been patented as U.S. Pat. No. 8,357,652.

BACKGROUND

The present disclosure is related to making and using fibrillar human serum albumin. (HSA) Fibrillar HSA was shown to cause apoptosis of many types of cancer cells by modulating the Akt signaling pathway, as disclosed in U.S. Pat. No. 7,488,800, which is incorporated by reference.

SUMMARY

Fibrillar human serum albumin was shown to be effective in the treatment of various types of cancers. Methods and compositions are disclosed for using fibrillar human serum albumin as a medicament to treat subjects having cancer.

According to a feature of the present disclosure, a composition is disclosed comprising fibrillar human serum albumin and a pharmaceutically acceptable carrier.

According to a feature of the present disclosure, a method is disclosed comprising administering to a subject having cancer a therapeutically effective amount of fibrillar human serum albumin.

According to a feature of the present disclosure, a method is disclosed comprising manufacturing a composition useful in the treatment of cancer, the medication comprising fibrillar human serum albumin and a pharmaceutically acceptable carrier.

According to a feature of the present disclosure, a method is disclosed comprising providing a therapeutically effective amount of fibrillar serum albumin for use in a subject having cancer.

According to a feature of the present disclosure, a method is disclosed comprising dissolving HSA in an SDS solution; applying the dissolved HSA through a gel filtration column with a pore size of at least about 70 kDa; removing the HSA from the column; and dialyzing the solution against phosphate buffered saline to remove the SDS.

DRAWINGS

The above-mentioned features and objects of the present disclosure will become more apparent with reference to the following description taken in conjunction with the accompanying drawings wherein like reference numerals denote like elements and in which:

FIGS. 11A-11C are implementations of experimental data showing the effect of F-HSA in suppressing the metastasis of mouse breast tumor MDA-MB-231 cells to the lung.

DETAILED DESCRIPTION

Figure 1:
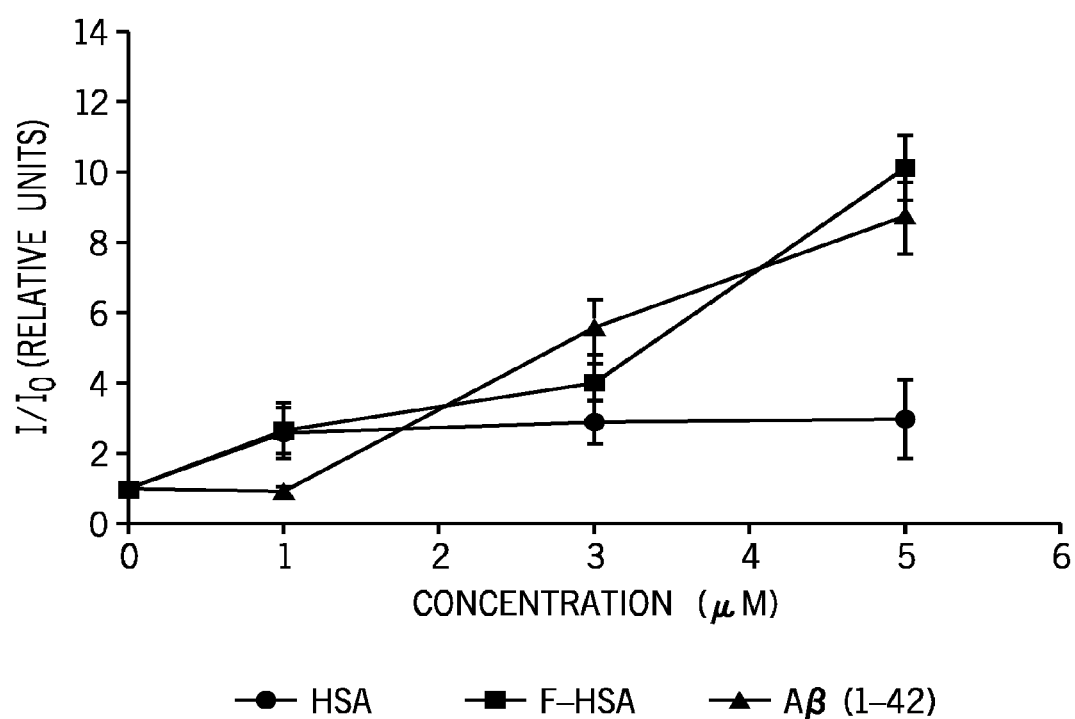
FIG. 1 is an implementation of experimental data showing a comparison of fluorescence level of increasing concentrations of F-HSA, HSA, and A β (1-42) after incubating with 20 μM amyloid-specific dye ThT for 1 h.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

This application incorporates by reference U.S. Patent Application Publication No. 2008/0300186, published Dec. 4, 2009.

The present disclosure relates to a process of producing fibrillar proteins and methods of treatment using fibrillar proteins. This process has advantages which include ease of control, homogeneity of production, and feasibility of scaling up. Moreover, fibrillization of proteins can be induced by this process without the assistance of fibril seed. Even a tiny amount of protein would be applicable to this process. As used herein, "protein" includes one or more proteins, protein fragments, polypeptides, or peptides. Proteins include both synthetic and naturally occurring proteins.

According to the present disclosure, a method is disclosed for changing a globular protein structure into a fibrillar protein structure. The method can be used to convert native proteins, regardless of their sequence, into fibrillar form in a simple and rapid manner. The method comprises the steps of dissolving a globular protein in a solution that contains detergents and applying the solution to a molecular sizing column that can separate proteins of 70 kDa molecular weight or larger, and eluting the protein with a solution containing detergent.

In an exemplary implementation, the method comprises the steps of providing a globular protein, forming a solution containing the globular protein, adding a detergent to the solution containing the globular protein, and applying the solution to a molecular sizing column with a pore size of at least 70 kDa.

In an exemplary implementation, the method comprises the steps of providing a globular protein, forming a solution containing the globular protein, adding a detergent to the solution containing the globular protein, and applying the solution to a molecular sizing column with a pore size of at least about 70 kDa in the presence of low concentration of detergent.

Globular proteins, also known as spheroproteins, are one of two main tertiary structure classes of proteins. Globular proteins are generally soluble and form spheriodal molecules in water. They have a complex secondary structure comprising a mixture of secondary structure motifs, such as α-helices, β-sheets, and loop structures. The other main tertiary structure class of proteins are fibrillar proteins, or fibrous proteins. Fibrillar proteins are generally insoluble and have an elongated shape. They have a simpler secondary structure and are often based on only one type of secondary structure motif.

Surfactants, also referred to herein as detergents, are substances that lower the surface tension of water and increase the solubility of organic compounds. Detergents may be ionic, which includes cationic, anionic, and zwitterionic detergents, as well as non-ionic. Detergents play a role in disrupting non-covalent bonds in proteins, thereby denaturing the proteins such that they lose their native shape or conformation. In exemplary implementations, the detergent used is sodium dodecyl sulfate (SDS), obtained from Sigma. In other exemplary implementations, the detergent used is Zwittergent 3-14, obtained from Calbiochem.

Amyloids are fibrous cross-β protein aggregates. Numerous proteins are capable of converting to amyloid-like fibrils with characteristics that include fibrillar morphology, protofilament substructure, cross-β diffraction pattern, an increase in β-structure, Congo red binding, and ThT binding. In exemplary implementations, the globular protein is converted to form amyloid-like fibrils, which allows for the converted protein to be identified by its amyloid-like properties.

According to implementations, chromatography may be used in the process to convert the globular protein structure into a fibrillar protein structure and separate them. Generally, chromatography is accomplished using columns, though other methods such as those used for thin-layer chromatography may also be possible. Chromatography techniques include size exclusion, affinity, and ion-exchange. Though a batch-type production of fibrillar proteins is possible, utilizing a column process allows globular proteins to be converted into a fibrillar form in a rapid, steady, efficient, and continuous manner. Scaling-up this process is also possible with the usage of columns.

According to exemplary implementations, size exclusion chromatography with bead pore sizes of at least about 70 kDa is used. The bead pore size used may vary depending on various characteristics of the globular protein, for example its size. The pore size plays a role in allowing proteins to enter the bead matrix, thus leading to mechanical forces which contribute to protein unfolding/folding and enhance fibrillogenic ensemble. In exemplary implementations, the molecular sizing column used is a Superdex 200. In other exemplary implementations, the molecular sizing column used is a HW55S.

For column chromatography, a buffer solution containing low concentration(s) of detergent may be used to elute the column. In exemplary implementations, the molecular sizing column is eluted with a buffer solution containing 25 mM Tris-HCl (pH 8.0), 1 mM EDTA, 0.1 M NaCl, and 0.05% SDS. In other exemplary implementations, the molecular sizing column is eluted with a buffer solution containing 25 mM Tris-HCl, pH 8.0, 1 mM EDTA, 0.1 M NaCl, and 0.05% Zwittergent 3-14. The eluant may be collected as fractions and the fractions containing the fibrillar protein subsequently pooled together. The pooled fraction may then be further filtered to purify and isolate the fibrillar protein, for example dialyzing against PBS to remove SDS or Zwittergent 3-14.

According to implementations, human serum albumin (HSA) can be made into fibrillar human serum albumin by the processes disclosed herein for creating fibrillar proteins. According to implementations, human serum albumin has been confirmed convert to fibrillar form by the processes disclosed herein. With respect to creating fibrillar proteins, U.S. Pat. No. 7,488,800 is incorporated by reference.

The fibrillar HSA (F-HSA) was unexpectedly found to be at least as potent as recombinant capsid protein of foot and mouth disease virus (rVP1) in causing apoptosis in a variety of cancer cells. Among the advantages of using F-HSA instead of rVP1 as a cancer therapeutic is that HSA is a human endogenous protein. Thus, HSA or its derivatives with similar sequence and composition would be less likely than foreign proteins such as rVP1 to induce immunogenicity and neutralizing antibodies during clinical applications.

According to implementations, F-HSA was generated by dissolving HSA in a 1% SDS solution, passing through a Superdex-200 gel filtration column and eluting with a buffer solution containing 25 mM Tris-HCl (pH 8.0), 1 mM EDTA, 0.1 M NaCl, and 0.05% SDS (FIG. 1). After dialysis against PBS to remove the SDS, it was found that unlike HSA, the eluted F-HSA from the Superdex-200 column exhibited enhanced fluorescence level of amyloid-specific dye ThT in a dose-dependent manner (FIG. 1).

It was then determined that F-HSA induced cytotoxicity in cancer cells. As fibrillar serum albumin bound to receptors such as integrins on the cell surface while globular serum albumin could not, it is believed that the change of structure of serum albumin from globular to fibrillar form has enabled the proteins to selectively target cancer cells that expressed more integrin α5β1 than normal cells. F-HSA inhibited breast cancer cell growth dose dependently including TS/A (murine mammary adenocarcinoma) and MDA-MB-231 (human mammary adenocarcinoma) cells with $IC_{50}$ of 0.15 (FIG. 2) and 0.48 μM (FIG. 3), respectively. F-HSA inhibited ovarian cancer cell SKOV3 growth with $IC_{50}$ of 0.6 μM (FIG. 4) and cervical cancer cell CaSki growth with $IC_{50}$ of 1.1 μM (FIG. 5). F-HSA also induced cytotoxicity in prostate cancer cells PC-3 and 22Rv1 with $IC_{50}$ of 0.35 (FIG. 6) and 0.2 μM (FIG. 7), respectively. In addition, F-HSA induces cytotoxicity in a number lung cancer cell lines (FIG. 8).

According to implementations, therefore, a method for treating cancer is disclosed. The method comprises the steps of providing HSA, changing the HSA into a fibrillar structure, and administering a therapeutically effective amount of the F-HSA to a patient in need thereof. Conversion of the HSA into fibrillar form increases its cytotoxic effects on target cells.

In exemplary implementations, the cancer is a kidney, breast, lung, prostate, liver, cervical, or ovarian cancer. In exemplary implementations, the fibrillar HSA plays a role in inducing cancer cell apoptosis by modulating the Akt signaling pathway. In some instances, the fibrillar HSA modulates integrin α5β1 or αvβ3 which leads to the deactivation of Akt. In other instances, fibrillar HSA binds to integrin and causes cellular apoptosis mainly through the integrin/FAK/Akt/GSK-3β/caspase-3 pathway.

The fibrillar HSA protein, derivate, ortholog, or other protein having substantial identity to HSA for treating the cancer may be selected based on the severity of the disease and the desired cytotoxicity to the cancer cells. In exemplary implementations, for greater cytotoxicity to the cancer cells, a protein with an RGD motif or greater molecular weight is selected. RGD motif is a ligand for integrins. It has been shown that fibrillar proteins induced cell death via modulating integrin/Akt signaling pathway. It has been found that fibrillar proteins with RGD motifs, like rVP1-S200 and FN-S200, were more cytotoxic than those without RGD motifs such as BSA-S200 and rVP3-S200.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions, and truncations in the polypeptide encoded by the reference sequence, as discussed herein.

A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

An "ortholog" denotes a polypeptide or polynucleotide obtained from another species that is the functional counterpart of a polypeptide or polynucleotide from a different species. Sequence differences among orthologs are the result of speciation.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleuci-ne, phenylalanine-tyrosine, lysine-arginine, alanine-valine, glutamic-aspartic, and asparagine-glutamine.

As discussed herein, minor variations in the amino acid sequences of compositions having cytotoxic activities are contemplated as being encompassed by the present invention, providing that the variations in the amino acid of HSA sequence maintain at least 75%, at least 80%, at least 90%, at least 95%, or at least 99% identity. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Fragments or analogs of proteins or peptides of the present invention can be readily prepared by those of ordinary skill in the art. Preferred amino- and carboxy-termini of fragments or analogs occur near boundaries of functional domains. Structural and functional domains can be identified by comparison of the nucleotide or amino acid sequence data to public or proprietary sequence databases. Preferably, computerized comparison methods are used to identify sequence motifs or predicted protein conformation domains that occur in other proteins of known structure or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Effective amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

The term "polypeptide fragment" as used herein refers to a polypeptide that has an amino-terminal or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long.

Pharmaceutical or Nutraceutical Compositions

According to another aspect of this disclosure, fibrillar HSA can be included in a pharmaceutical or nutraceutical composition together with additional active agents, carriers, vehicles, excipients, or auxiliary agents identifiable by a person skilled in the art upon reading of the present disclosure.

The pharmaceutical or nutraceutical compositions preferably comprise at least one pharmaceutically acceptable carrier. In such pharmaceutical compositions, the fibrillar HSA or fibrillar HSA equivalent forms the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, intraperitoneal, intraarterial, intramuscular, intralesional, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

"Subject" as used herein refers to humans and non-human primates (e.g. guerilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer), and any other organisms who can benefit from the agents of the present disclosure. There is no limitation on the type of animal that could benefit from the presently described agents. A subject regardless of whether it is a human or non-human organism may be referred to as a patient, individual, animal, host, or recipient.

Pharmaceutical compositions suitable for an injectable (or an infusion) include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor® EL (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. According to embodiments, isotonic agents, for example, sugars, polyalcohols such as manitol, sorbitol, or sodium chloride in the composition are added. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preparation is prepared by vacuum drying or freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or strawberry, cherry, grape, lemon, or orange flavoring.

For administration by inhalation, the compounds are delivered in the form of an aerosol spray from pressured container or dispenser which contains a suitable propellant, e.g., a gas such as carbon dioxide, or a nebulizer.

According to embodiments, intravitreal injection is accomplished using PLGA-based microparticles or nanoparticles (liposomes). PEG-based formulas may also be used.

Accordingly, the other methods for injectable pharmaceutical compositions are expressly contemplated for intravitreal injection.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In addition to the other forms of delivery, the compounds are deliverable via eye drop or intraocular injection. With respect to eye drops, the compositions of the present disclosure optionally comprise one or more excipients intended for topical application to the eye or nose. Excipients commonly used in pharmaceutical compositions intended for topical application to the eyes, such as solutions or sprays, include, but are not limited to, tonicity agents, preservatives, chelating agents, buffering agents, surfactants and antioxidants. Suitable tonicity-adjusting agents include mannitol, sodium chloride, glycerin, sorbitol and the like. Suitable preservatives include p-hydroxybenzoic acid ester, benzalkonium chloride, benzododecinium bromide, polyquaternium-1 and the like. Suitable chelating agents include sodium edetate and the like. Suitable buffering agents include phosphates, borates, citrates, acetates and the like. Suitable surfactants include ionic and nonionic surfactants, though nonionic surfactants are preferred, such as polysorbates, polyethoxylated castor oil derivatives and oxyethylated tertiary octylphenol formaldehyde polymer (tyloxapol). Suitable antioxidants include sulfites, ascorbates, BHA and BHT. The compositions of the present disclosure optionally comprise an additional active agent. With the exception of the optional preservative ingredient (e.g., polyquaternium-1), the compositions of the present disclosure preferably do not contain any polymeric ingredient other than polyvinylpyrrolidone or polystyrene sulfonic acid.

When the compositions of the present disclosure contain polyvinylpyrrolidone, the polyvinylpyrrolidone ingredient is preferably selected or processed to minimize peroxide content. Freshly produced batches of polyvinylpyrrolidone are preferred over aged batches. Additionally, particularly in cases where the composition will contain greater than 0.5% polyvinylpyrrolidone, the polyvinylpyrrolidone ingredient should be thermally treated (i.e., heated to a temperature above room temperature) prior to mixing with olopatadine in order to reduce the amount of peroxides in the polyvinylpyrrolidone ingredient and minimize the effect of peroxides on the chemical stability of olopatadine. While thermally treating an aqueous solution of polyvinylpyrrolidone for prolonged periods will substantially reduce the amount of peroxides, it can lead to discoloration (yellow to yellowish-brown) of the polyvinylpyrrolidone solution. In order to substantially reduce or eliminate peroxides without discoloring the polyvinylpyrrolidone solution, the pH of the aqueous solution of polyvinylpyrrolidone should be adjusted to pH 11-13 before it is subjected to heat. Much shorter heating times are needed to achieve significant reductions in peroxide levels if the pH of the polyvinylpyrrolidone solution is elevated.

One suitable method of thermally treating the polyvinylpyrrolidone ingredient is as follows. First, dissolve the polyvinylpyrrolidone ingredient in purified water to make a 4-6% solution, then raise the pH of the solution to pH 11-13, (an effective range of pH is 11-11.5), then heat to a temperature in the range of 60-121° C., preferably 65-80° C. and most preferably 70-75° C. The elevated temperature should be maintained for approximately 30-120 minutes (preferably 30 minutes). After the heated solution cools to room temperature, add HCl to adjust the pH to 3.5-8, depending upon the target pH for the olopatadine composition.

Particularly for compositions intended to be administered as eye drops, the compositions preferably contain a tonicity-adjusting agent in an amount sufficient to cause the final composition to have an ophthalmically acceptable osmolality (generally 150-450 mOsm, preferably 250-350 mOsm). The ophthalmic compositions of the present disclosure preferably have a pH of 4-8, preferably a pH of 6.5-7.5, and most preferably a pH of 6.8-7.2.

The eye-drop compositions of the present disclosure are preferably packaged in opaque plastic containers. A preferred container for an ophthalmic product is a low-density polyethylene container that has been sterilized using ethylene oxide instead of gamma-irradiation.

With respect to opthamalic injectables, the pharmaceutical compositions of this disclosure are administered to the area in need of treatment by subconjunctival administration. One preferred method of subconjunctival administration to the eye is by injectable formulations comprising the pharamaceutical compositions disclosed herein. Another preferred method of subconjunctival administration is by implantations comprising slow releasing compositions.

Compositions that are delivered subconjunctivally comprise, according to embodiments, an ophthalmic depot formulation comprising an active agent for subconjunctival administration. According to embodiments, the ophthalmic depot formulation comprises microparticles of essentially pure active agent. The microparticles comprising can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g., by gelifying or precipitating.

Solid articles suitable for implantation in the eye can also be designed in such a fashion to comprise polymers and can be bioerodible or non-bioerodible. Bioerodible polymers that can be used in preparation of ocular implants carrying the compositions of the present disclosure include without restriction aliphatic polyesters such as polymers and copolymers of poly(glycolide), poly(lactide), poly(ε-caprolactone), poly(hydroxybutyrate) and poly(hydroxyvalerate), polyamino acids, polyorthoesters, polyanhydrides, aliphatic polycarbonates and polyether lactones. Illustrative of suitable non-bioerodible polymers are silicone elastomers.

According to embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the invention. The therapeutic effect may include, for example but not by way of limitation, being substantially cytotoxic to cancer cells, but less cytotoxic to natural cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

EXAMPLES

A more complete understanding of the present disclosure can be obtained by reference to the following specific examples and figures. The examples and figures are described solely for purposes of illustration and are not intended to limit the scope of the disclosure. Changes in form and substitution of equivalents are contemplated as circumstances may suggest or render expedient. Although specific terms have been employed herein, such terms are intended in a descriptive sense and not for purposes of limitations. Modifications and variations of the disclosure as hereinbefore set forth can be made without departing from the spirit and scope thereof, and, therefore, only such limitations should be imposed as are indicated by the appended claims.

Example 1

F-HSA Exhibits Enhanced Fluorescence Levels of Amyloid-Specific Dye ThT in a Dose-Dependent Manner FIG. 1 is an implementation of experimental data shows that F-HSA, like amyloid fibrils A β (1-42), exhibit enhanced fluorescence level of amyloid-specific dye ThT in a dose-dependent manner as compared with BSA not processed by the Superdex-200 column. This result shows that F-HSA has a fibrillar structure like A β (1-42), whereas HSA has a globular structure. (Binding to ThT is one of the characteristics of amyloid-like proteins.)

Example 2

F-HSA has a Cytotoxic Effect on Prostate Cancer Cells

Figure 2:
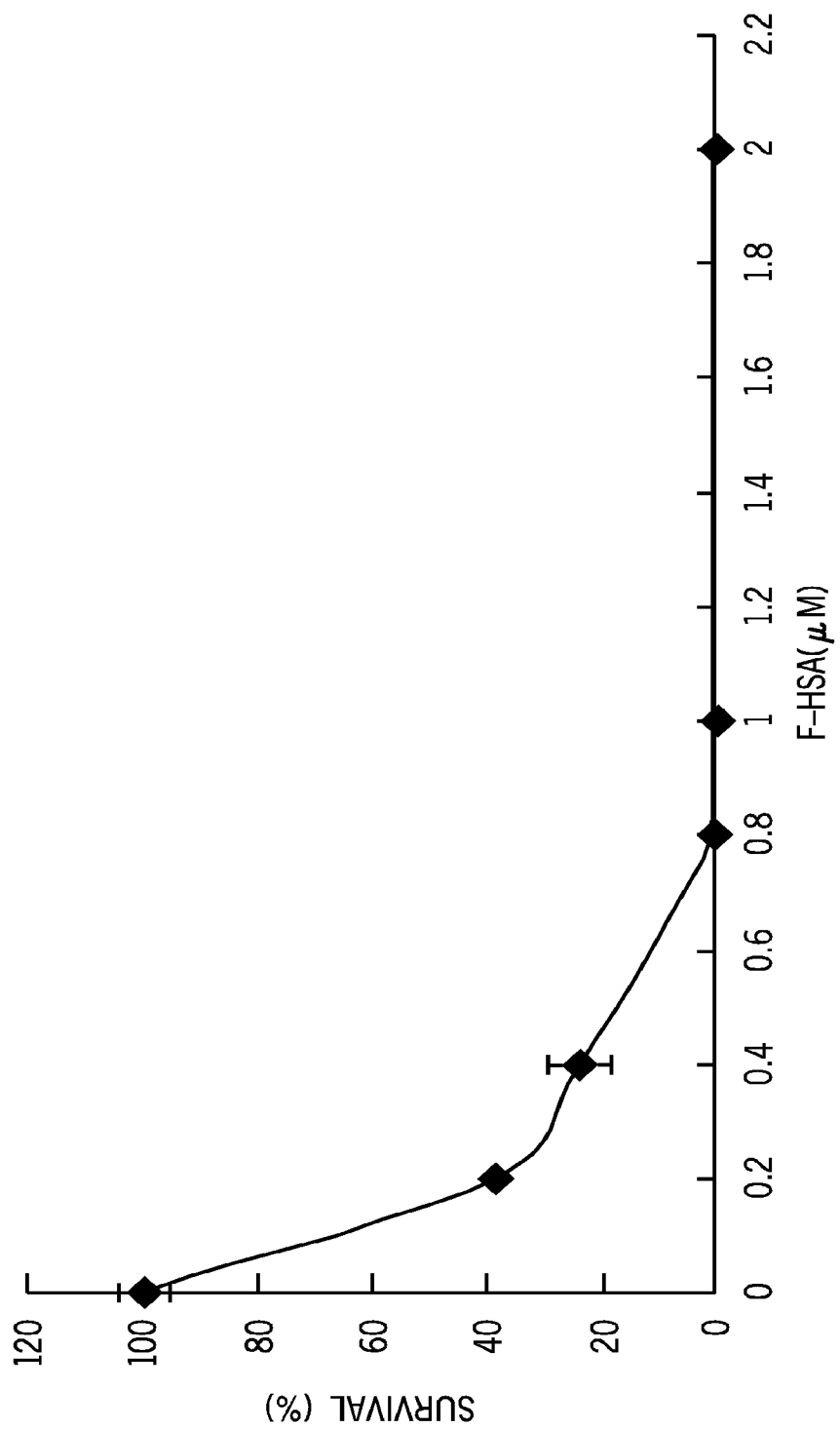
FIG. 2 is an implementation of experimental data showing the cytotoxic effects of F-HSA on breast cancer cells.
Figure 3:
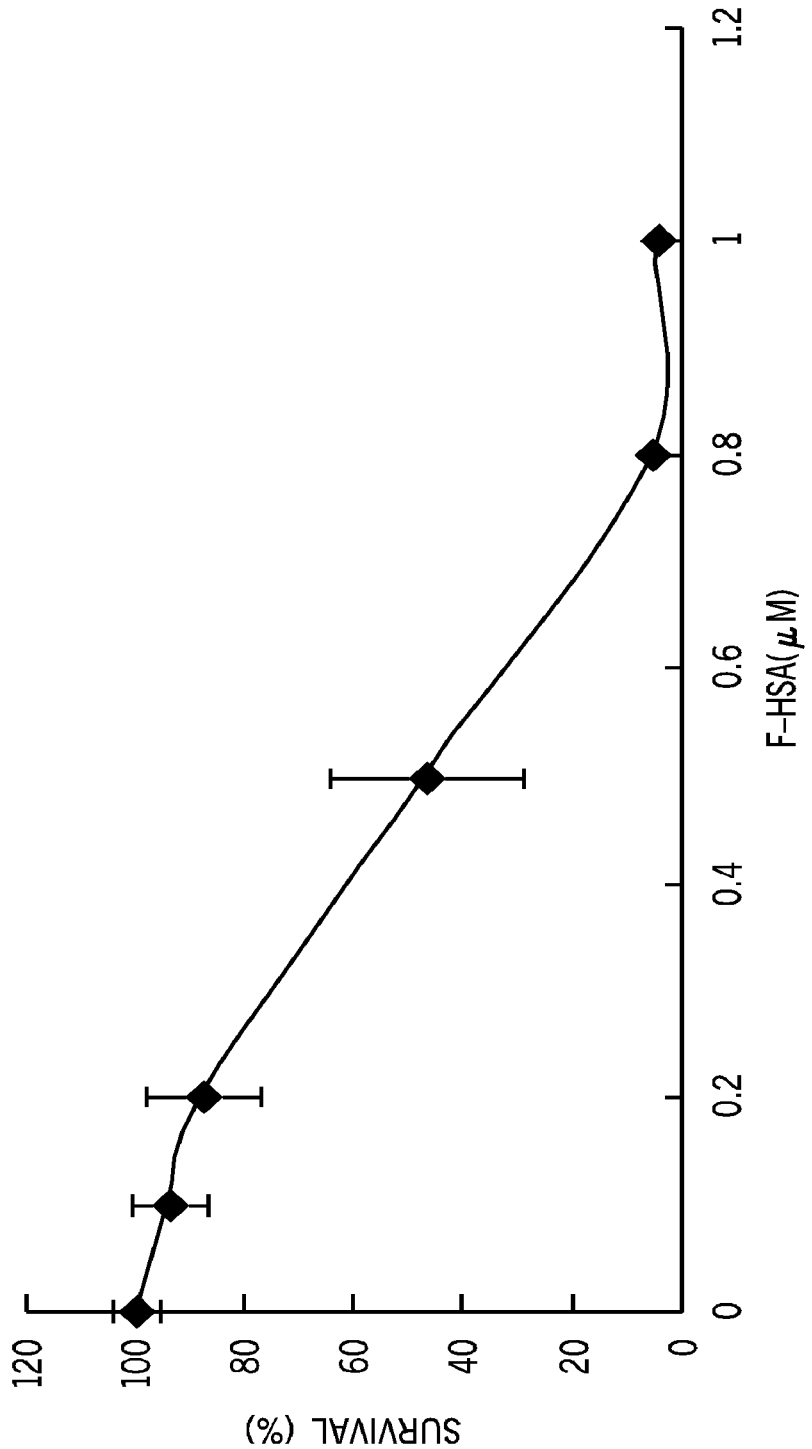
FIG. 3 is an implementation of experimental data showing the cytotoxic effects of F-HSA on breast cancer cells.

FIG. 2 shows F-HSA's cytotoxic effect in TS/A cells and FIG. 3 shows F-HSA's cytotoxic effect in MDA-MB-231 cells. Each respective cell type was treated for 16 h in serum-free culture medium with various concentrations of F-HSA. Cell viability was determined by the MTT assay. Globular HSA has no cytotoxic effect on normal or cancer cells.

Example 3

F-HSA has a Cytotoxic Effect on Prostate Cancer Cells

Figure 4:
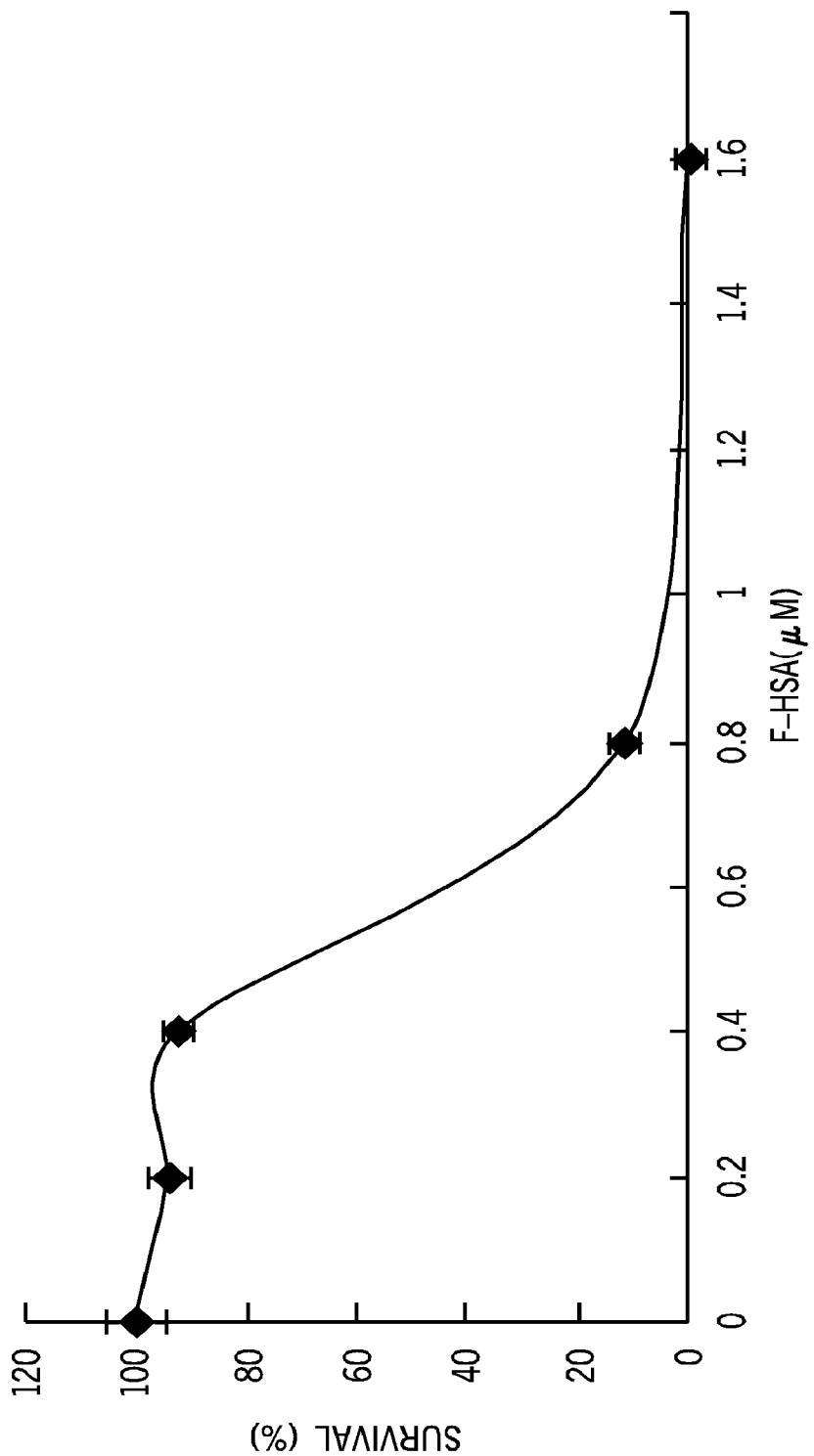
FIG. 4 is an implementation of experimental data showing the cytotoxic effects of F-HSA on ovarian cells.
Figure 5:
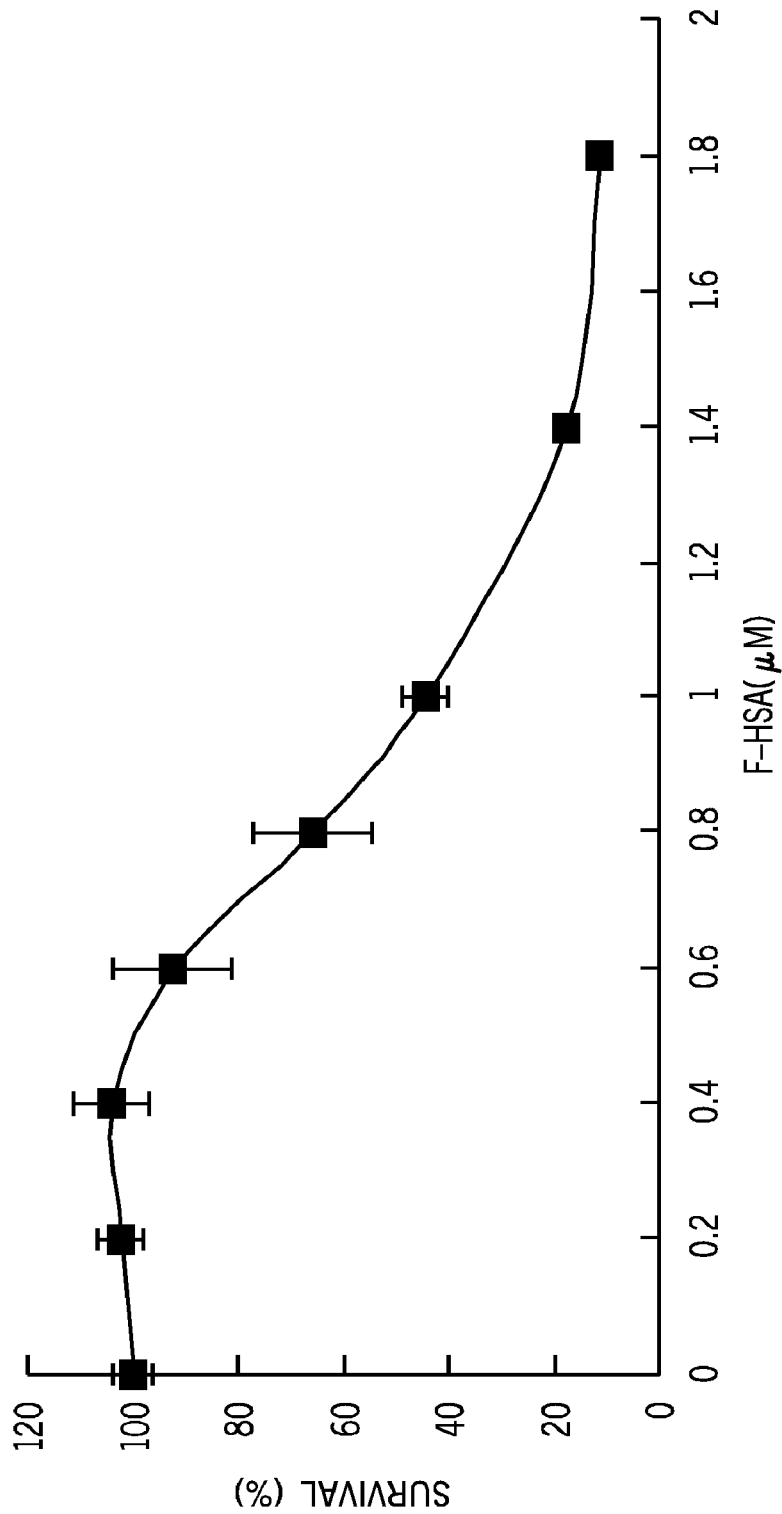
FIG. 5 is an implementation of experimental data showing the cytotoxic effects of F-HSA on cervical cancer cells.

FIG. 4 shows F-HSA's cytotoxic effect in SKOV-3 cells and FIG. 5 shows F-HSA's cytotoxic effect in CaSki cells. Each respective cell type was treated for 16 h in serum-free culture medium with various concentrations of F-HSA. Cell viability was determined by the MTT assay.

Example 4

F-HSA has a Cytotoxic Effect on Prostate Cancer Cells

Figure 6:
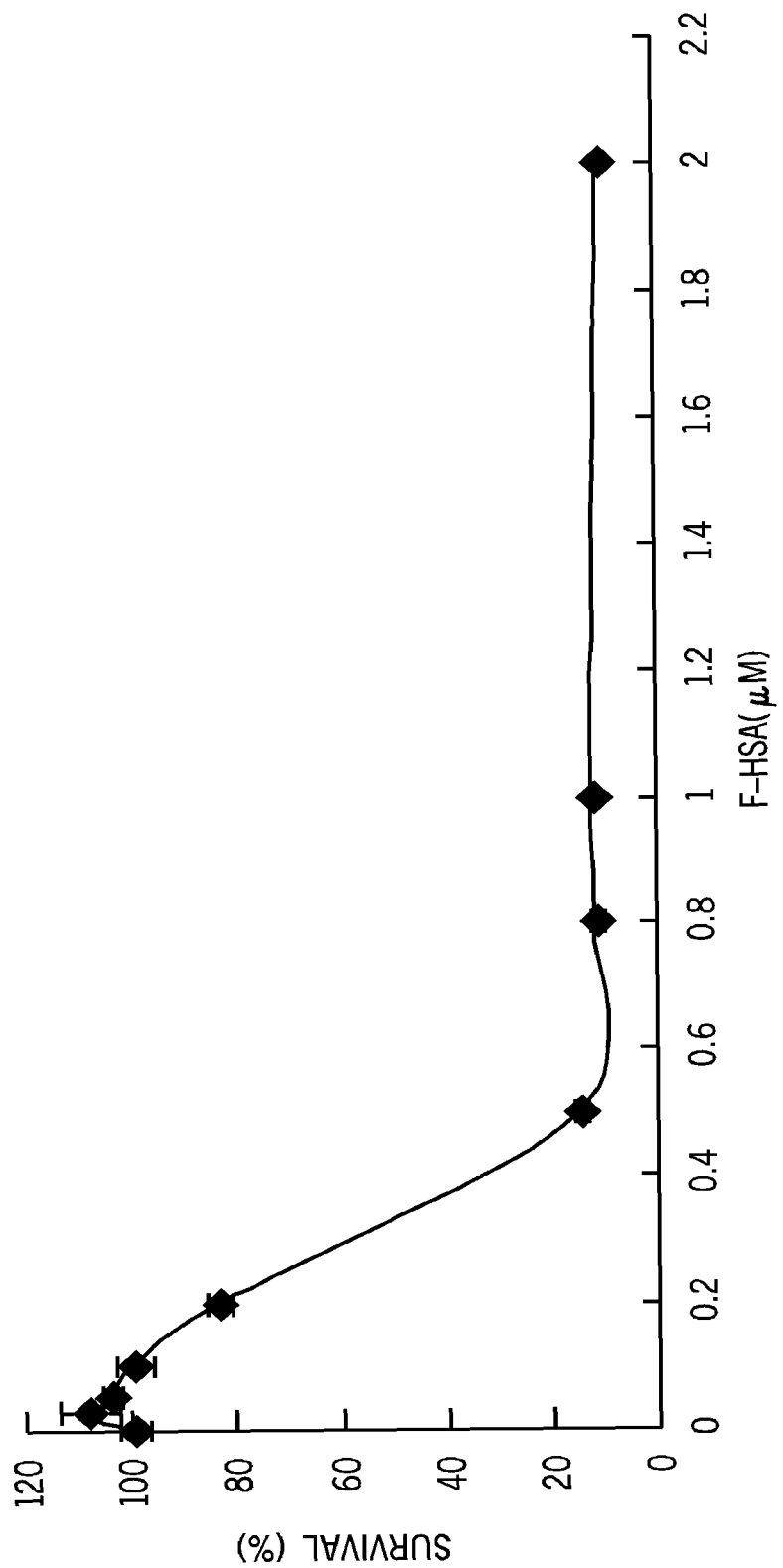
FIG. 6 is an implementation of experimental data showing the cytotoxic effects of F-HSA on prostate cancer cells.
Figure 7:
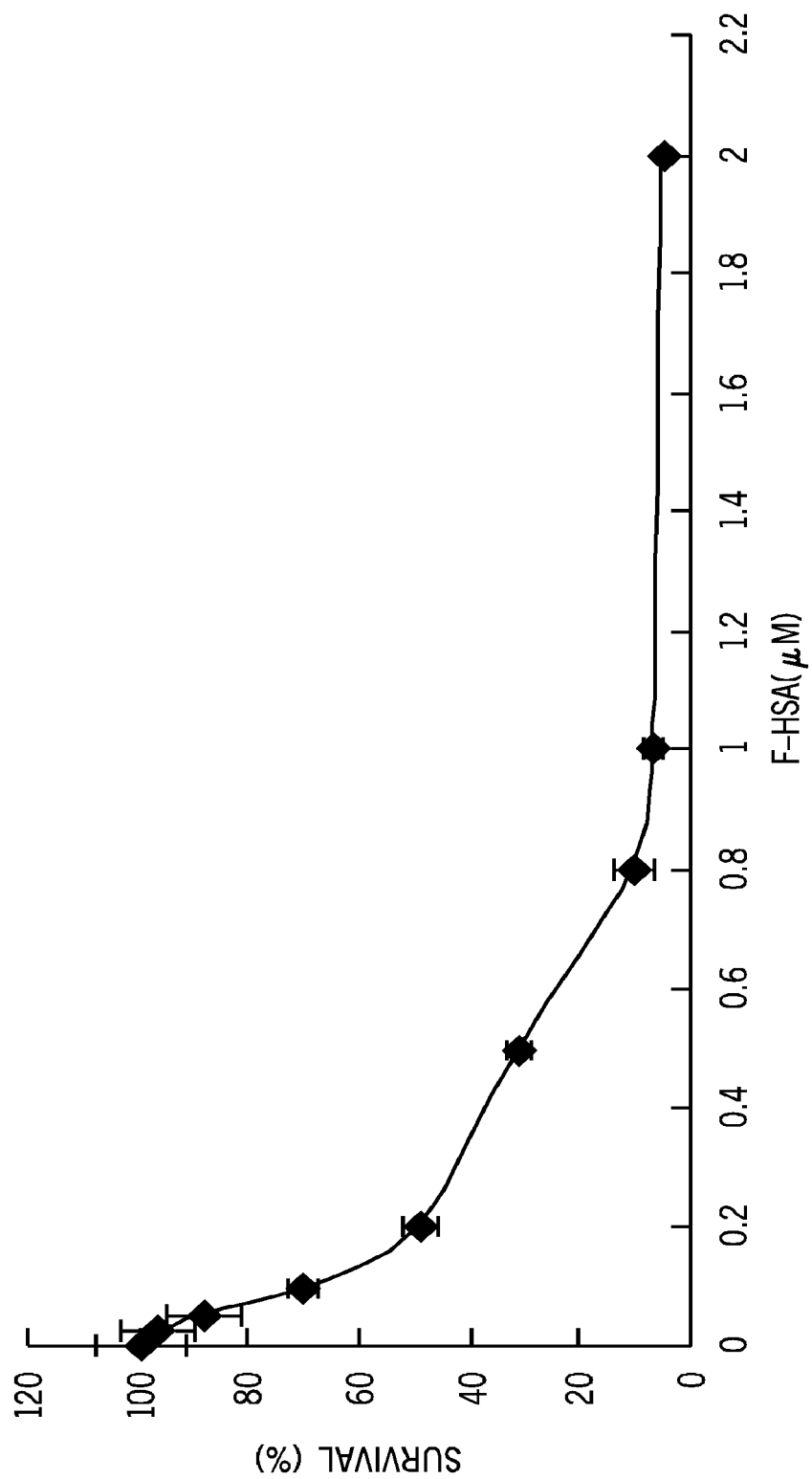
FIG. 7 is an implementation of experimental data showing the cytotoxic effects of F-HSA on prostate cancer cells.
Figure 8:
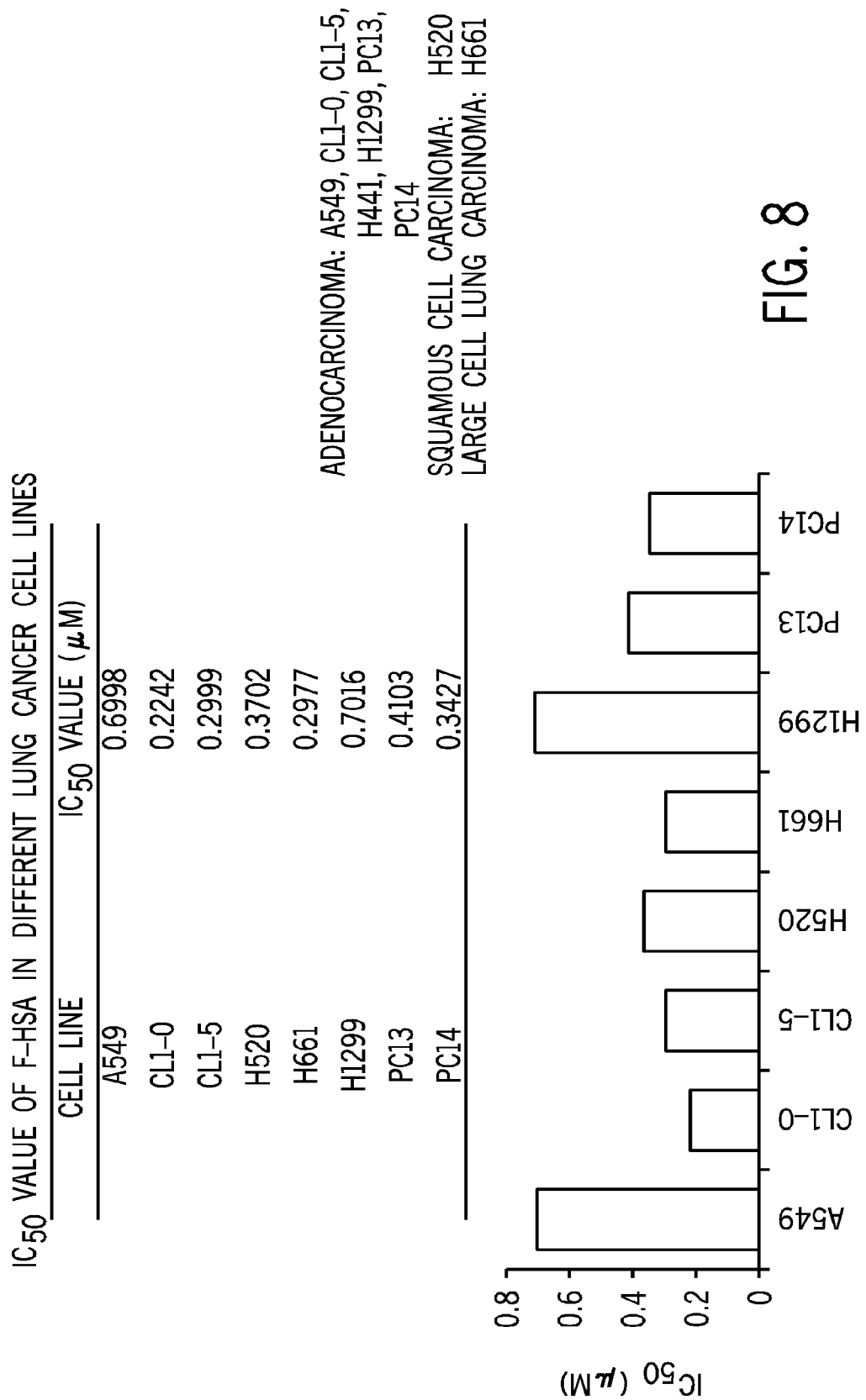
FIG. 8 is an implementation of experimental data showing the cytotocix effects of F-HSA on lung cancer cells.
Figure 9A:
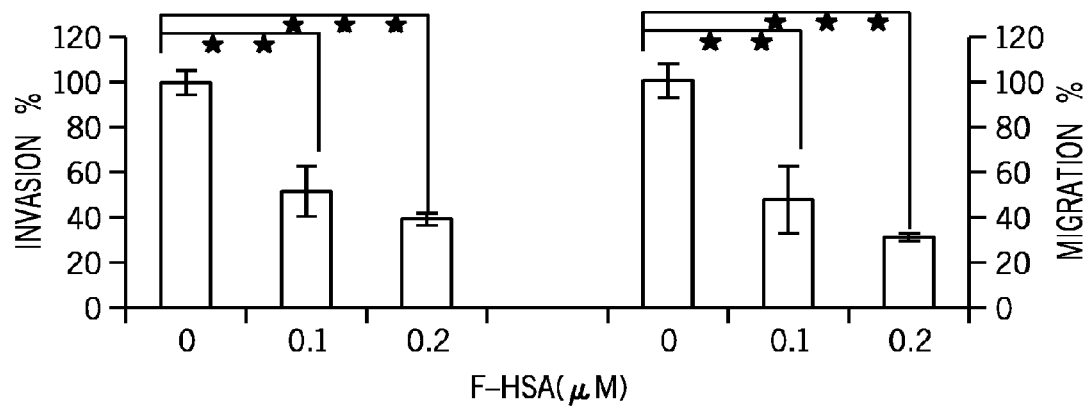
FIGS. 9A-9H are implementations of experimental data showing the effect of F-HSA in reducing the rate of tumor cell migrations and invasion without effecting viability of normal cells.
Figure 9B:
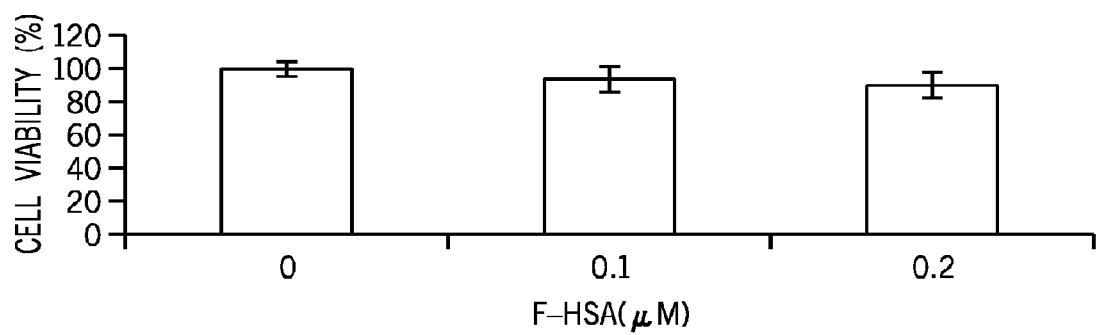
Figure 9C:
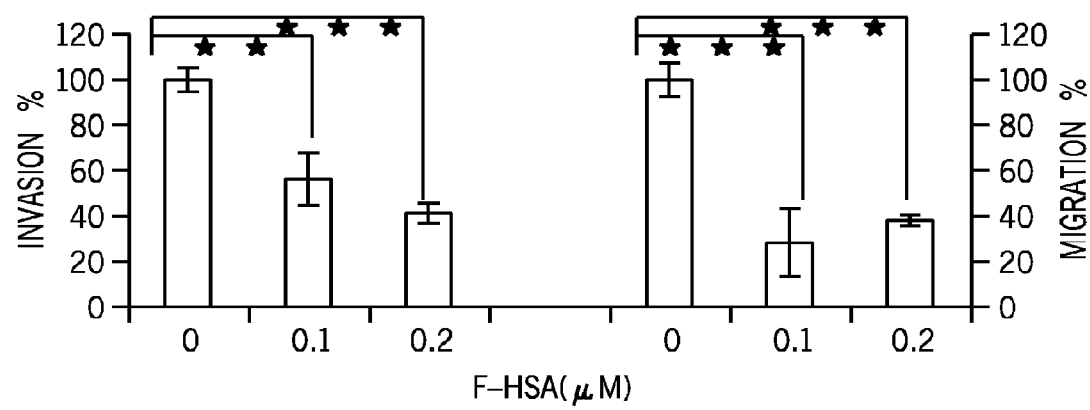
Figure 9D:
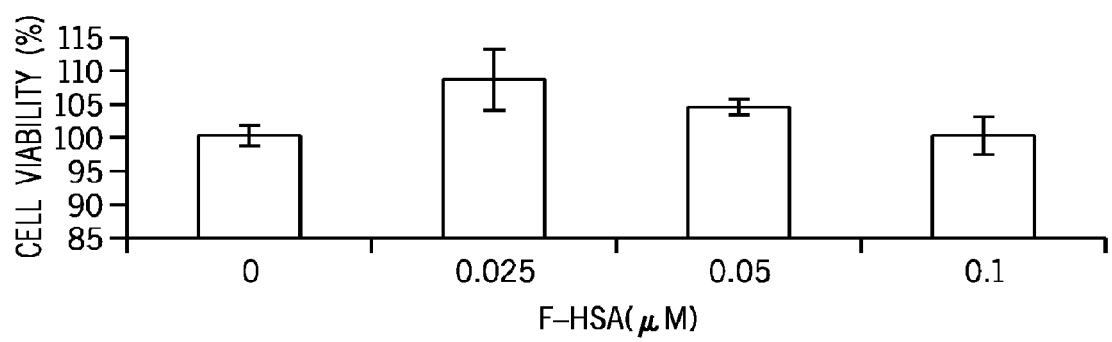
Figure 9E:
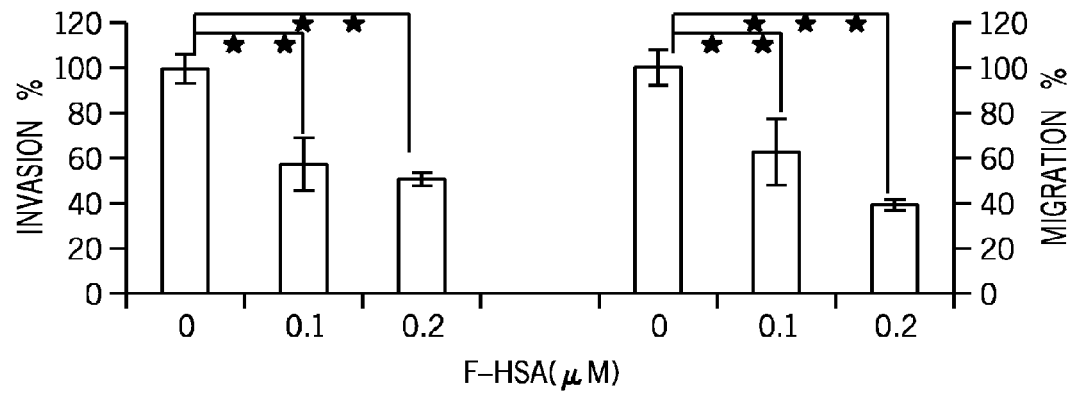
Figure 9F:
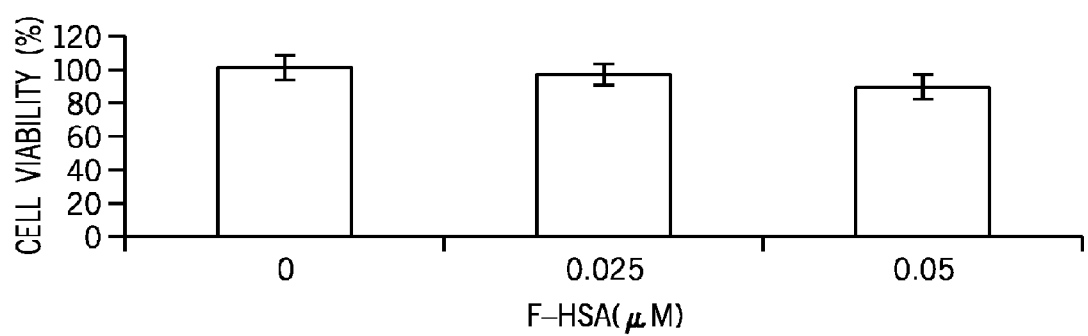
Figure 9G:
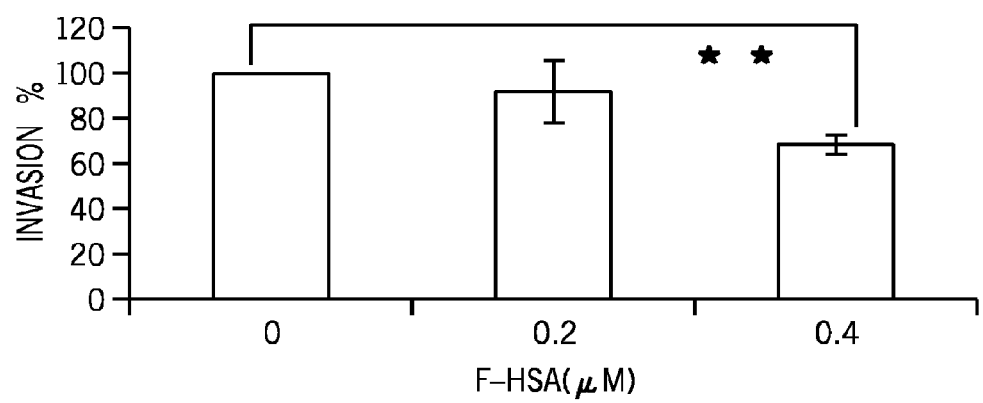
Figure 9H:
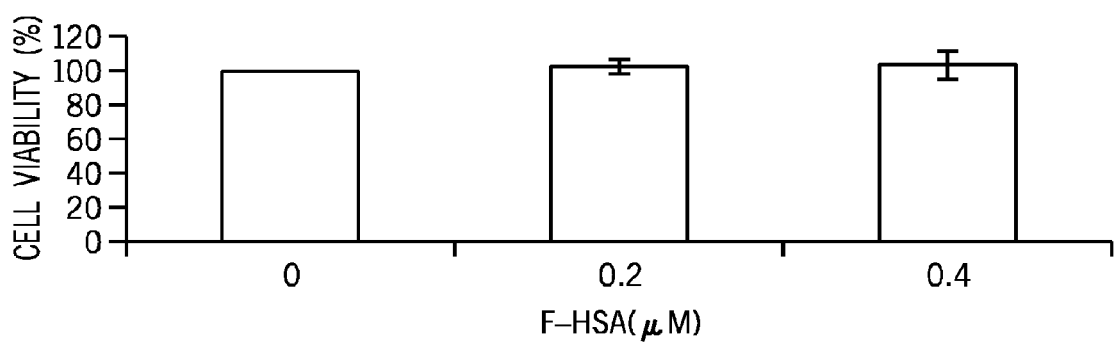

FIG. 6 shows F-HSA's cytotoxic effect in PC-3 cells and FIG. 7 shows F-HSA's cytotoxic effect in 22 Rv1 cells. The respective cell type was treated for 16 h in serum-free culture medium with various concentrations of F-HSA. Cell viability was determined by the MTT assay.

Example 5

F-HSA has a Cytotoxic Effect on Lung Cancer Cell Lines

According to implementations shown in FIG. 8, F-HSA was shown to induce cytotoxicity in adenocarcinoma cell lines A549, CL1-0, Cl1-5, H1299, PC13, and PC14; squamous cell carcinoma lung cancer cell line H520, and large cell lung cancer carcinoma cell line H661. FIG. 8 shows the $IC_{50}$ of each of the respective cell lines.

Example 6

F-HSA Suppresses Tumor Cell Invasion and Migration In Vitro

F-HSA was also shown to be effective in suppressing tumor cell invasion and migration in vitro, as shown according to implementations of experimental data in FIG. 9. As shown in FIGS. 9A, 9C, 9E, and 9G, F-HSA significantly reduced the tumor cells invasion/migration abilities, at concentrations which did not affect viability of either cancer or normal cells.

Example 7

F-HSA Suppressed Tumor Cell Metastasis In Vivo

Figure 10B:
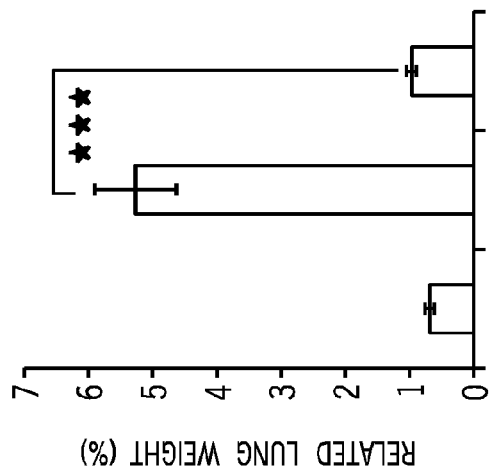
FIGS. 10A-10C are implementations of experimental data showing the effect of F-HSA in suppressing the metastasis of mouse breast tumor TS/A cells to the lung.
Figure 10C:
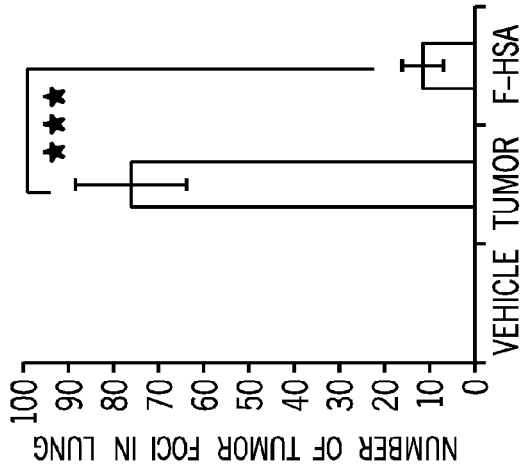
Figure 10A:
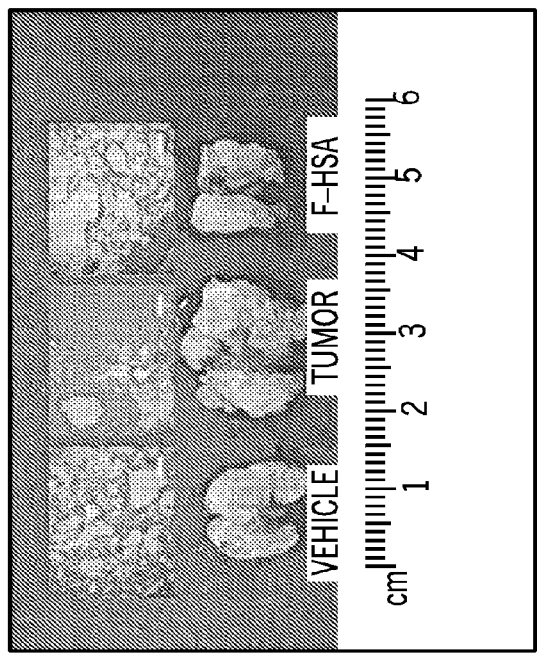

F-HSA suppressed breast cancer tumor cell lines TS/A and MDA-MB-231 in vivo. Breast cancer cells were injected via the tail vein of the subjects. Tumor cell foci detected in the lung tissue indicated that the breast cancer cells had metastasized into lung. FIGS. 10A and 11A show F-HSA significantly suppressed the metastasis of breast cancer TS/A cells and MDA-MB-231 cells to lung compared with TS/A or MDA-MB-231 bearing mice without F-HSA treatment. FIGS. 10B, 10C, 11B, and 11C measure the weight and the number of tumor cell foci in the lung tissues, which further confirmed the efficacy of F-HSA in vivo.

Example 8

Materials and Methods

Preparation of F-HSA.

Twenty milligrams of HSA was dissolved in 10 ml of PBS with 1% SDS (w/v). The HSA solution was sonicated for 5 min and subsequently applied to a Superdex-200, which was previously equilibrated with the eluting solution (25 mM Tris-HCl (pH 8.0), 1 mM EDTA, 0.1 M NaCl, and 0.05% SDS). The column was eluted at the rate of 1 ml/min and fractions C3 to C7 that contained HSA were pooled. The pooled fractions were concentrated to 2~3 mg/ml then dialyzed against PBS with Cellu-Sep T4/Nominal (MWCO: 12,000-14,000 Da) dialysis membrane. New PBS buffer was exchanged every two hours at room temperature three times. The yield of the HSA-S200 was about 75%.

Thioflavin T (ThT) Fluorescence Assay.

Binding to ThT is one of the characteristics of amyloid-like proteins. For fluorescence measurements, increasing concentrations of proteins were incubated with 20 µM ThT for 1 h at room temperature, the fluorescence was then measured in triplicate on a Wallac Victor$^2$ 1420 Multilabel Counter (Perkin Elmer Life Science, Waltham, Mass., USA). Excitation and emission wavelengths were 430 nm and 486 nm, respectively. ThT background signal from buffer solution was subtracted from corresponding measurements.

Cell Survival was Determined by MTT Colorimetric Assay.

Exponentially growing cells ($2\times10^4$ cells/well for TS/A) were seeded in a 96-well plate in medium with 10% FBS and incubated for 24 h. Treatment of cells with a series of concentrations of proteins was carried out in serum-free medium for 16 hr indication at 37° C. After treatment, MTT solution was added to each well (0.5 mg/ml), followed by a 4 h incubation period. The viable cell number is directly proportional to the production of formazan, which, following solubilization with isopropanol, can be measured spectrophotometrically at 570 nm by an ELISA plate reader.

Cell Viability Assays.

Cell viability was measured by WST-1 assay according to the manufacturer's instructions (Roche, Mannheim, Germany). In brief, $2\times10^4$ cells were added to 100 µl media per well on a 96 well plate and incubated at 37° C. in 5% $CO_2$ overnight in a humidified incubator. The cells attached to the wells were incubated in serum-free medium and treated with various concentrations of F-HSA. After incubation at 37° C. in 5% $CO_2$ for 16 h to allow the drug to take effect, 10 µl WST-1 reagent was added to each well. The plate was then placed onto a shaking table and shaken at 150 rpm for 1 min. After incubation at 37° C. in 5% $CO_2$ for another 2 h to allow the WST-1 reagent to be metabolized, the proportion of surviving cells were determined by optical density (450 nm test wavelength, 690 nm reference wavelength). The percentage of surviving cells was calculated as (O.D. treatment/O.D. control)×100% while the percentage of growth inhibition was calculated as [1−(O.D. treatment/O.D. control)]×100%. According to this experiment, $IC_{50}$ is the concentration at which the reagent yields 50% inhibition of the cellular viability.

Cell Migration and Invasion Assays.

Cell migration and invasion were determined by using Boyden chamber migration and invasion assay (Corning). In brief, the 8-µm pore membranes of the upper chambers were coated with 20 µg/ml fibronectin (for cell migration assay) or 40 µg/ml Matrigel (for cell invasion assay) and placed in a well with 1 ml of PBS and incubated for 2 h at 37° C. Cancer cells ($1\times10^5$) in 100 µl of serum free culture medium were seeded in the upper chamber for 1 h. A serially diluted concentration of F-HSA was added into the upper chamber and then the culture medium containing 10% FBS was added to the lower chamber. Cells were incubated for 24 h at 37° C. After incubation, cells on the upper side of the membrane were removed by wiping it with a cotton swab, and cells that had migrated onto the lower membrane surface were dissociated by using cell dissociation solution (Sigma) and counted by flow cytometer (BD company). At these concentrations, however, F-HSA did not affect cell viability when measured with the MTT assay, and as shown in FIGS. 9B, 9D, 9F, and 9H. Viability and cytotoxicity was measured using MTT or WST-1 assay. These kits are designed for the spectrophotometric measurement of cell growth as a function of mitochondrial activity in living cells (Roche).

Breast Cancer Cell Metastasation In Vivo.

TS/A murine mammary adenocarcinoma cells were intravenously injected into the lateral tail vein of BALB/c mice or MDA-MB-231 human mammary adenocarcinoma cells were injected into nude mice. F-HSA (1 mg/kg) was then injected intravenously at next day and then one time every two days for ten times. At the end of F-HSA treatment, mice were sacrificed to detect the metastasis of lungs.

While the method and agent have been described in terms of what are presently considered to be the most practical and preferred implementations, it is to be understood that the disclosure need not be limited to the disclosed exemplary implementations it is apparent that modifications and adaptations of those implementations will occur to those skilled in the art. It is intended to cover various modifications and similar arrangements included within the spirit and scope of the claims, the scope of which should be accorded the broadest interpretation so as to encompass all such modifications and similar structures. The present disclosure includes any and all implementations of the following claims.

The invention claimed is:

1. A composition comprising:
   fibrillar human serum albumin and a pharmaceutically acceptable carrier wherein the human serum albumin is produced by a method comprising:
   dissolving human serum albumin in a suitable detergent
   sonicating the human serum albumin
   applying the sonicated human serum albumin to a gel filtration column with a separation range above 70 kDA molecular weight; so as to promote column-induced fibrillar protein formation and to separate globular protein from fibrillar protein;
   eluting the fibrillar human serum albumin from the column with a buffer containing a low concentration of detergent;
   collecting eluent containing fibrillar human serum albumin from the column, and
   dialyzing the eluent to remove the detergent.

* * * * *